(12) United States Patent
Siewerdsen et al.

(10) Patent No.: US 11,669,984 B2
(45) Date of Patent: Jun. 6, 2023

(54) METHOD AND SYSTEM FOR REGISTERING MULTIPLE STRUCTURES IN MEDICAL IMAGES

(71) Applicants: THE JOHNS HOPKINS UNIVERSITY, Baltimore, MD (US); Siemens Healthcare GmbH, Erlangen (DE)

(72) Inventors: Jeffrey H. Siewerdsen, Baltimore, MD (US); Runze Han, Baltimore, MD (US); Gerhard Kleinszig, Forchheim (DE); Sebastian Vogt, Monument, CO (US)

(73) Assignees: THE JOHNS HOPKINS UNIVERSITY, Baltimore, MD (US); SIEMENS HEALTHCARE GMBH, Erlangen (DE)

( * ) Notice: Subject to any disclaimer, the term of this patent is extended or adjusted under 35 U.S.C. 154(b) by 169 days.

(21) Appl. No.: 17/175,125

(22) Filed: Feb. 12, 2021

(65) Prior Publication Data
US 2021/0256716 A1 Aug. 19, 2021

Related U.S. Application Data

(60) Provisional application No. 62/976,771, filed on Feb. 14, 2020.

(51) Int. Cl.
*G06T 7/33* (2017.01)
*A61B 34/10* (2016.01)
(Continued)

(52) U.S. Cl.
CPC .............. *G06T 7/344* (2017.01); *A61B 34/10* (2016.02); *G06T 7/11* (2017.01); *G06T 7/337* (2017.01);
(Continued)

(58) Field of Classification Search
CPC . G06T 7/337; G06T 7/11; G06T 17/00; G06T 19/20; G06T 2207/10081;
(Continued)

(56) References Cited

PUBLICATIONS

Gong et al., "Multiple-Object2-D-3-D Registration for Noninvasive Pose Identification of Fracture Fragments," IEEE Transactions on Biomedical Engineering, vol. 58, No. 6, Jun. 2011, p. 1592-1601 (Year: 2011).*

(Continued)

*Primary Examiner* — Sing-Wai Wu
(74) *Attorney, Agent, or Firm* — MH2 Technology Law Group LLP

(57) ABSTRACT

A method, computer system, and a computer-readable medium for registering one or more structures to a desired orientation for planning and guidance for surgery is provided. The method includes in a preoperative stage, obtaining one or more 3D models of one or more structures from one or more CT images using an image processing segmentation technique or a manual segmentation technique; in the preoperative stage, registering the one or more structures to a template that is adapted to an alternating registration for a patient-specific shape and pose for a desired reduction and corresponding reduction transformations; in an intraoperative stage, mapping the one or more structures to one or more radiographs via a 3D-2D registration that iteratively optimizes a similarity metric between acquired and simulated radiographs; and in the intraoperative stage, providing an output that is representative of a radiograph or a 3D tomographic representation to provide guidance to a user.

20 Claims, 5 Drawing Sheets

(51) Int. Cl.
  G06T 7/11    (2017.01)
  G06T 17/00   (2006.01)
  G06T 19/20   (2011.01)
  A61B 34/20   (2016.01)
  A61B 90/00   (2016.01)
  G06T 7/35    (2017.01)

(52) U.S. Cl.
  CPC .............. *G06T 17/00* (2013.01); *G06T 19/20* (2013.01); *A61B 34/20* (2016.02); *A61B 2034/102* (2016.02); *A61B 2034/105* (2016.02); *A61B 2090/367* (2016.02); *A61B 2090/3762* (2016.02); *G06T 2207/10081* (2013.01); *G06T 2207/10124* (2013.01); *G06T 2207/30008* (2013.01); *G06T 2210/41* (2013.01); *G06T 2219/2004* (2013.01)

(58) Field of Classification Search
  CPC . G06T 2207/10121; G06T 2207/10124; G06T 2207/30008; G06T 2210/41; G06T 2219/2004; G06T 7/344; G06T 7/35; A61B 2034/102; A61B 2034/105; A61B 2090/364; A61B 2090/367; A61B 2090/376; A61B 2090/3762; A61B 34/10; A61B 34/20
  See application file for complete search history.

(56) References Cited

PUBLICATIONS

Albrecht et al., "Posterior shape models", Medical Image Analysis, (2013), vol. 17, pp. 959-973.
Albrecht et al., "Automatic fracture reduction (including subseries Lecture Notes in Artificial Intelligence and Lecture Notes in Bioinformatics)", LNCS, (2012), 7599, pp. 22-29.
Bossa et al., "Statistical Model of Similarity Transformations: Building a Multi-Object Pose Model of Brain Structures", Proceedings of the 2006 Conference on Computer Vision and Pattern Recognition Workshop, (2006), pp. 1-8.
Byrd et al., "A trust region method based on interior point techniques for nonlinear programming", Mathematical Programming, (2000), vol. 89, pp. 149-185.
Cootes et al., "Active Shape Models-Their Training and Application", Computer Vission and Image Understaning, Jan. 1995, vol. 61, No. 1, pp. 38-59.
De Silva et al., "3D-2D image registration for target localization in spine surgery: investigation of similarity metrics providing robustness to content mismatch", Physics in Medicine & Biology, (2016), vol. 61, pp. 3009-3025.
De Silva et al., "Registration of MRI to Intraoperative Radiographs for Target Localization in Spinal Interventions", Phys. Med. Biol., Jan. 21, 2017, vol. 62 No 2, pp. 684-701.
Fletcher et al., "Principal Geodesic Analysis for the Study of Nonlinear Statistics of Shape", IEEE Transactions on Medical Imaging, Aug. 2004, vol. 23, No. 8, pp. 995-1005.
Furnstahl et al., "Computer assisted reconstruction of complex proximal humerus fractures for preoperative planning", Medical Image Analysis, (2012), vol. 16, No. 3, p. 704-720.
Han et al., "Atlas-based automatic planning and 3D-2D fluoroscopic guidance in pelvic trauma surgery", Physics in Medicine & Biology, (2019), 64, 095022, 18 pages.
Han et al., "Multi-body 3D-2D registration for image-guided reduction of pelvic dislocation in orthopaedic trauma surgery", Physics in Medicine & Biology, (2020), vol. 65, 135009, 20 pages.
Han et al., "Multi-Body Registration for Fracture Reduction in Orthopaedic Trauma Surgery", Proc. SPIE, (2020), vol. 11315, pp. 113150F-1-113150F-7.
Han et al., "Fracture reduction planning and guidance in orthopaedic trauma surgery via multi-body image registration", Medical Image Analysis, (2021), vol. 68, 101917, 18 pages.
Hansen et al., "Reducing the Time Complexity of the Derandomized Evolution Strategy with Covariance Matrix Adaptation (CMA-ES)", Evolutionary Computation, (2003), vol. 11 No. 1, pp. 1-18.
Lowe, "Distinctive Image Features from Scale-Invariant Keypoints", International Journal of Computer Vision, (2004), vol. 60, No. 2, pp. 91-110.
Luthi et al., "Gaussian Process Morphable Models", IEEE Transactions on Pattern Analysis and Machine Intelligence, Aug. 2018, vol. 40, No. 8, pp. 1860-1873.
Okada et al., "Computer-Assisted Preoperative Planning for Reduction of Proximal Femoral Fracture Using 3-D-CT Data", IEEE Transactions On Biomedical Engineering, Mar. 2009, vol. 56, No. 3, pp. 749-759.
Otake et al., "Robust 3D-2D image registration: application to spine interventions and vertebral labeling in the presence of anatomical deformation", Physics in Medicine and Biology, (2013), vol. 58, pp. 8535-8553.
Rueckert et al., "Automatic Construction of 3-D Statistical Deformation Models of the Brain Using Nonrigid Registration", IEEE Transactions on Medical Imaging, Aug. 2003, vol. 22, No. 8, pp. 1014-1025.
Schweizer et al., "Complex Radius Shaft Malunion: Osteotomy with Computer-Assisted Planning", Hand, (2010), vol. 5, pp. 171-178.
Steihaug, "The Conjugate Gradient Method and Trust Regions in Large Scale Optimization*", SIAM J. Numer. Anal., Jun. 1983, vol. 20, No. 3, pp. 626-637.
Uneri et al., "3D-2D registration for surgical guidance: effect of projection view angles on registration accuracy", Physics in Medicine and Biology, (2014), vol. 59, pp. 271-287.
Yuan et al., "A Study on Continuous Max-Flow and Min-Cut Approaches", Proceedings of the IEEE Computer Society Conference on Computer Vision and Pattern Recognition, (2010), pp. 2217-2224.
Yuan et al., A Continuous Max-Flow Approach to Potts Model (including subseries Lecture Notes in Artificial Intelligence and Lecture Notes in Bioinformatics), LNCS, (2010), 6316, 14 pages.
Schnabel et al., "A Generic Framework for Non-rigid Registration Based on Non-uniform Multi-level Free-Form Deformations", MICCAI 2001, 9 pages (2001).
Vidal et al., "Generalized Principal Component Analysis", Interdisciplinary Applied Mathematics, vol. 40, 2016, 590 pages.

* cited by examiner

302
DRR Edges

304
Reduction Plan

METHOD AND SYSTEM FOR REGISTERING MULTIPLE STRUCTURES IN MEDICAL IMAGES

CROSS REFERENCE TO RELATED APPLICATIONS

This application claims priority to U.S. Provisional Patent Application No. 62/976,771 filed on Feb. 14, 2020, the disclosure of which is hereby incorporated by reference in its entirety.

FIELD

This disclosure relates generally to method and systems for registering multiple structures in medical images.

SUMMARY

In accordance with examples of the present disclosure, a method for registering one or more structures to a desired orientation for planning and guidance for surgery is disclosed. The method comprises in a preoperative stage, obtaining one or more 3D models of one or more structures from one or more CT images using an image processing segmentation technique or a manual segmentation technique; in the preoperative stage, registering the one or more structures to a template that is adapted to an alternating registration for a patient-specific shape and pose for a desired reduction and corresponding reduction transformations; in an intraoperative stage, mapping the one or more structures to one or more radiographs via a 3D-2D registration that iteratively optimizes a similarity metric between acquired and simulated radiographs; and in the intraoperative stage, providing an output that is representative of a radiograph or a 3D tomographic representation to provide guidance to a user.

In some examples, the one or more structures comprise one or more anatomical structures, an anatomy with multiple components, one or more anatomical structures and one or more surgical instruments, and combinations thereof. The multiple components can comprise one or more bone fragment components.

In some examples, the template is based on a statistical shape model and a statistical pose model.

In some examples, the output comprises a 2D x-ray image, such as a 2D fluoroscopic scene or a 3D shape representation of the anatomy as evident in the 2D x-ray view.

In some examples, the registering comprises computing a cost function for multi-body registration based on a disparity between the template and positions of the one or more structures.

In some examples, the one or more structures comprise multiple bone fragments of a pelvis and the cost function is computed based on a disparity between a pelvis template and the multiple bone fragments.

In some examples, the one or more structures comprise multiple bones comprising a joint and the cost function is computed based on a disparity between a template of the joint and the multiple bone components.

In some examples, the cost function is further computed based on a fragment collision regularization.

In some examples, the disparity is a squared difference.

In some examples, the image processing segmentation techniques comprises a max-flow min-cut segmentation technique.

In accordance with examples of the present disclosure, a computer system is provided. The computer system comprises a hardware processor; a non-transitory computer readable medium comprising instructions that when executed by the hardware processor perform a method for registering one or more structures to a desired orientation for planning and guidance for surgery, the method comprising: in a preoperative stage, obtaining one or more 3D models of one or more structures from one or more CT images using an image processing segmentation technique or a manual segmentation technique; in the preoperative stage, registering the one or more structures to a template that is adapted to an alternating registration for a patient-specific shape and pose for a desired reduction and corresponding reduction transformations; in an intraoperative stage, mapping the one or more structures to one or more radiographs via a 3D-2D registration that iteratively optimizes a similarity metric between acquired and simulated radiographs; and in the intraoperative stage, providing an output that is representative of a radiograph or a 3D tomographic representation to provide guidance to a user.

Various examples of the computer system can include one or more of the following features. The one or more structures comprise one or more anatomical structures, an anatomy with multiple components, one or more anatomical structures and one or more surgical instruments, and combinations thereof. The multiple components comprise one or more bone fragment components. The template is based on a statistical shape model and a statistical pose model. The output comprises a 2D x-ray, such as a 2D fluoroscopic scene, or a 3D shape representation of the anatomy as evident in the 2D x-ray view (i.e., 2D fluoroscopy view). The registering comprises computing a cost function for multi-body registration based on a disparity between the template and positions of the one or more structures. The one or more structures comprise multiple bone fragments of a pelvis and the cost function is computed based on a disparity between a pelvis template and the multiple bone fragments. The cost function is further computed based on a fragment collision regularization. The disparity is a squared difference. The image processing segmentation techniques comprises a max-flow min-cut segmentation technique.

In accordance with examples of the present disclosure, a non-transitory computer readable medium is provided that comprises instructions that when executed by a hardware processor perform a method for registering one or more structures to a desired orientation for planning and guidance for surgery, the method comprising: in a preoperative stage, obtaining one or more 3D models of one or more structures from one or more CT images using an image processing segmentation technique or a manual segmentation technique; in the preoperative stage, registering the one or more structures to a template that is adapted to an alternating registration for a patient-specific shape and pose for a desired reduction and corresponding reduction transformations; in an intraoperative stage, mapping the one or more structures to one or more radiographs via a 3D-2D registration that iteratively optimizes a similarity metric between acquired and simulated radiographs; and in the intraoperative stage, providing an output that is representative of a radiograph or a 3D tomographic representation to provide guidance to a user.

Various examples of the non-transitory computer readable medium can include one or more the following features. The one or more structures comprise one or more anatomical structures, an anatomy with multiple components, one or more anatomical structures and one or more surgical instruments, and combinations thereof. The multiple components comprise one or more bone fragment components. The template is based on a statistical shape model and a statistical pose model. The output comprises a 2D x-ray view, such as a 2D fluoroscopic scene, or a 3D shape representation of the anatomy as evident in the 2D x-ray view. The registering comprises computing a cost function for multi-body registration based on a disparity between the template and positions of the one or more structures. The one or more structures comprise multiple bone fragments of a pelvis and the cost function is computed based on a disparity between a pelvis template and the multiple bone fragments. The cost function is further computed based on a fragment collision regularization. The disparity is a squared difference. The image processing segmentation techniques comprises a max-flow min-cut segmentation technique.

BRIEF DESCRIPTION OF THE DRAWINGS

Various features of the embodiments can be more fully appreciated, as the same become better understood with reference to the following detailed description of the embodiments when considered in connection with the accompanying figures, in which:

FIG. 3A shows an AP x-ray image, such as a fluoroscopic image, of a pelvis with left innominate fracture (two-body fracture at the ilium wing). The DRR Canny edges 302 of the two fragments, the right innominate and sacrum registration overlaid on the x-ray image, such as a fluoroscopic image, show close alignment. FIG. 3B shows the x-ray image, such as the fluoroscopic image, is augmented with a projection 304 of the preoperative reduction plan of the two fragments using the resulting 3D-2D registration. The current state of the patient relative to the target reduction and possible further reduction can be visualized. FIG. 3C shows a 3D visualization of the intraoperative bone positions 302 and 306 overlaid with the reduction planning 304.

DESCRIPTION OF THE EMBODIMENTS

Reference will now be made in detail to example implementations, illustrated in the accompanying drawings. Wherever possible, the same reference numbers will be used throughout the drawings to refer to the same or like parts. In the following description, reference is made to the accompanying drawings that form a part thereof, and in which is shown by way of illustration specific exemplary embodiments in which the invention may be practiced. These embodiments are described in sufficient detail to enable those skilled in the art to practice the invention and it is to be understood that other embodiments may be utilized and that changes may be made without departing from the scope of the invention. The following description is, therefore, merely exemplary.

Generally speaking, examples of the present disclosure provides a system and method for registration of multiple structures in the body between volumetric and projection images—so-called 3D-2D registration—to a desired geometrical pose using an adaptive template.

The "system and method" could refer to an intraoperative imaging system, such as a x-ray C-arm, such as a fluoroscopic C-arm, by which images of the body are obtained to guide treatment.

The term "registration" refers to the computation of spatial correspondence between to image coordinate systems. The "multiple structures" could be, for example, fractured bone fragments.

The "3D" and "2D" images could be volumetric CT and x-ray projection images, respectively.

The "desired geometrical pose" could refer to the intended orientation of the multiple structures—for example, reduction of the fracture to the natural morphology of the original (unfractured) bone and reduction of the dislocation to the natural morphology with respect to the surrounding bones. This is also referred to generally as a "reduction," below.

The "adaptive template" refers to a statistical template that can be adapted to patient-specific shapes and poses.

The scenario of pelvic trauma is considered throughout, but the invention may be generally applicable to a number of other scenarios—for example, registration of fracture fragments in other bones (e.g., the femur), the registration of other anatomy with multiple structures (e.g., the spine or a joint), or the registration of one or more anatomical structures and one or more interventional devices (e.g., the placement of one or more surgical instruments in one or more bone structures). For example, the disclosed method to register articulated bones such as the pelvis-femur, the femur-tibia, or the multiple bones comprising the ankle, etc. In some examples, the one or more structures comprise multiple bones comprising a joint and the cost function is computed based on a disparity between a template of the joint and the multiple bone components. For the remainder of this Detailed Description, the scenario of pelvic trauma is considered specifically.

Figure 1:
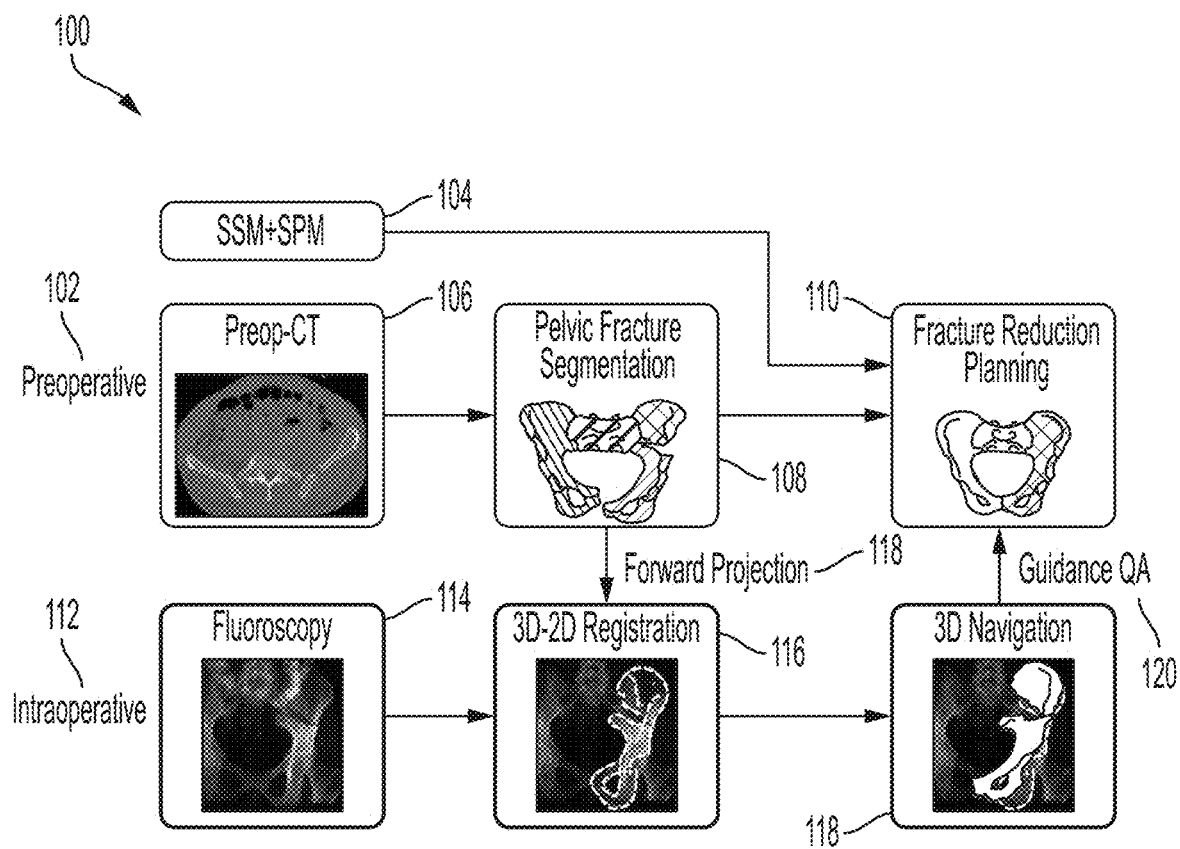
FIG. 1 shows a method and system flowchart for multiple structure reduction planning and x-ray (i.e., fluoroscopy) guidance, and the scenario of pelvic fracture reduction is illustrated. Preoperative steps 102 are in the top branch including elements 104, 106, and 110, and intraoperative steps 112 are in the bottom branch including 114, 116, and 118. The components of the algorithm comprise segmentation, fracture reduction planning, and fluoroscopy-guided navigation.
Figures 2A, 2B:
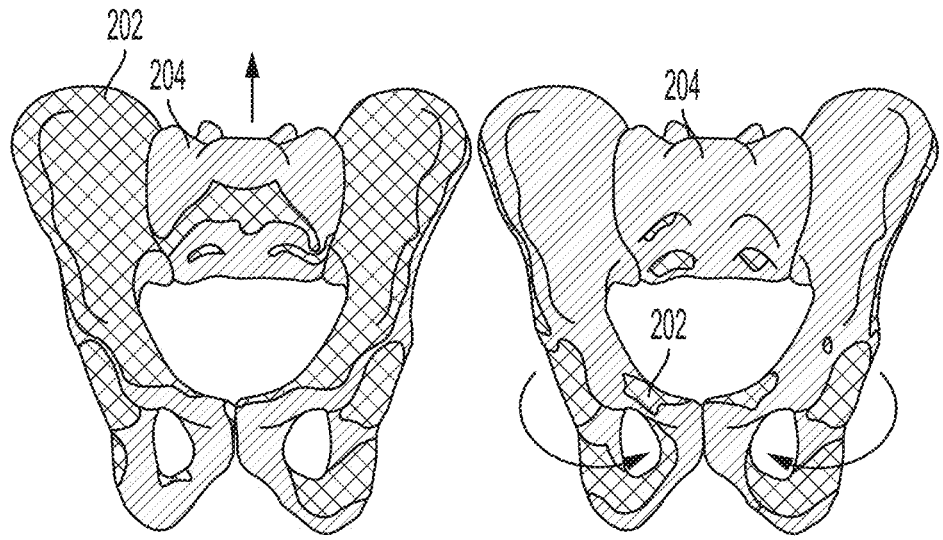
FIG. 2A, FIG. 2B, FIG. 2C, and FIG. 2D show a Statistical Pose Model (SPM) of the pelvis in four modes of variation (+3λ 202, −3λ 204) in pose of the sacrum and innominate bones according to examples of the present teachings.
Figures 2C, 2D:
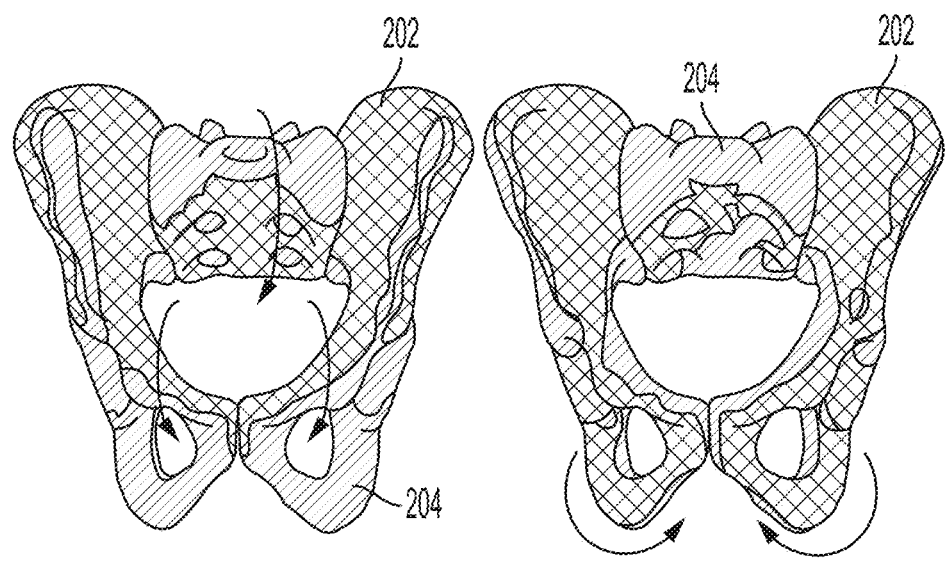

FIG. 1 shows a method 100 for image-guided fracture reduction for the specific case of pelvic trauma, according to examples of the present disclosure. The method 100 uses a two-stage process to: (1) Preoperative stage 102: compute the transformations of multiple bone fragments that restore bone morphology as a form of fracture reduction planning; and (2) Intraoperative stage 112: guide the reduction of bone fragments via 3D-2D registration and navigation with respect to x-ray, such as fluoroscopy, and/or preoperative CT.

The method 100 shown in FIG. 1 includes the following features, recognizing the possibility for alternative methods in particular sub-steps. The preoperative stage 102 uses a segmentation technique 108, such as a continuous max-flow min-cut segmentation (Yuan et al 2010a), to obtain 3D models of bone fragments 110 from a patient CT 1-6. The fragments are registered to an adaptive template (e.g., a combination of statistical shape model (SSM) and statistical pose model (SPM)) 104 using an alternating optimization for estimation of the desired reduction and the corresponding reduction transformations. The intraoperative stage 114 maps the multiple fragments imaged 114 using x-ray images, such as fluoroscopy or other suitable techniques, to one (or more) radiograph(s) via 3D-2D registration 116 that iteratively optimizes the image gradient similarity between the acquired and simulated radiographs (digitally reconstructed radiographs (DRR)) using a forward projection 118 from the segmentation technique 108. Once the 3D fragment poses are identified with respect to the CT and the reduction plan, the results can be visualized on a radiograph 118 to provide guidance 120 in a form that is familiar to orthopedic surgeons (i.e., the 2D x-ray image, such as a 2D fluoroscopic scene) or on the preoperative CT for 3D guidance analogous to conventional, tracker-based surgical navigation.

FIG. 2A, FIG. 2B, FIG. 2C, and FIG. 2D show a Statistical Pose Model (SPM) of the pelvis in four modes of variation (+3λ 202, −3λ 204) in pose of the sacrum and innominate bones according to examples of the present teachings.

An alternating registration framework to register bone fragment segmentations onto a template simultaneously and adapt the template to the patient-specific shapes and poses is provided. The specific scenario of pelvic reduction planning is illustrated. Aspects of the present disclosure provides the following advances. First, examples of the present disclosure provides for the combination of both shapes (SSM) and poses (SPM) into an adaptive template construction for multi-body reduction. Second, a cost function is provided for multi-body reduction planning (a many-to-one registration) by computing the squared difference between the pelvis template and multiple bone fragments and fragment collision regularization. An alternating optimization scheme is disclosed that iteratively solves for the fragment alignment and template adaptation. Third, the reduction planning is registered to the intraoperative space via 3D-2D multi-body to 2D x-ray image, such as fluoroscopy registration. The registration provides 3D localization of bone fragments and the respective pose of target reduction using a single 2D x-ray image, such as 2D fluoroscopy.

2.1 Fractured Bone Segmentation on CT Images

A semi-automatic segmentation method was implemented to segment bone fragments in preoperative CT images of fractured pelvis, requiring only an input "seed point" for each bone fragment of interest. The seed points are manually identified by the user clicking on a voxel within each bone fragment. The segmentation is formulated as an N-label continuous max-flow problem such that each bone fragment and the background are segmented into different labels, according to the cost function $$C_{seg}(x) = \min_u \quad (1)$$
$$f\left[\left(1 - \sum_n u_n(x)\right)D_1(x) + \beta \sum_{n=1}^{N} u_n(x)D_{2n}(x) + \gamma \sum_{n=1}^{N} g(x)|\nabla u_n(x)|\right]dx$$

such that $\sum_{n=1}^{N} u_n(x)=1$, $u_x(x) \geq 0$, where $u_n$, n=1, 2, ..., N is a membership function with value between 0 and 1 that defines whether a voxel x belongs to the n th label. A higher value represents a higher likelihood of the voxel belonging to the corresponding label. $D_1$ and $D_2$ are the costs of foreground and background voxels and are designed following (Han et al., 2020b). $D_1$ is the cost associated with the likelihood of the voxel being bone according to its CT Hounsfield unit (HU) and a priori intensity distribution learned from previous pelvis CT images. A gaussian mixture model with two components was chosen for the intensity distribution of pelvic bone (cortical and trabecular components). The distribution $D_2$ is the cost associated with the background voxels and is defined as the gradient-weighted distance from input seed points, which is higher when the path between the voxel and input seed points of the corresponding label traverses an image gradient (hence traversing a bone edge) and is therefore considered to be outside the bone.

The last term in the integrand of Eq. (1) is a regularization to enforce the smoothness of the segmentation by penalizing large segmentation gradient, $\nabla u(x)$:

$$g(x)=1+\exp(-\nabla I(x)) \quad (2)$$

where $\nabla I$ is the CT image gradient. $\beta$ and $\gamma$ are scalar parameters to control the relative strength of the three terms in the objective of Eq. (1). The N-label objective function was solved to obtain n−1 bone fragment segmentations S (n), n=1, 2, ..., N−1. In this work, $\beta$ and $\gamma$ were chosen to be 0.5 and 3.0, respectively, based on (Han et al., 2020b). The segmentation requires minimal user interaction, with as few as one seed point defined for each bone fragment in the CT image. In cases where two or more bone fragments are connected, additional seed points may be placed at the boundaries of the fragments.

2.2 Multi-Body 3D Registration for Fracture Reduction Planning 2.2.1 Statistical Shape Model of Anatomy in its Natural/Desired Morphology A statistical template of the pelvis is constructed to model multi-body bone shapes and poses, with adaptable shape and pose parameters to be adapted to patient-specific anatomy. This "adaptive template" serves as a fixed image onto which the segmentations of bone fragments are registered for fracture reduction planning. An open-source pelvis atlas (Han et al., 2019) comprised of 40 CT images and corresponding segmentations of left/right innominate bone (ilium, ischium, and pubis) and sacrum was used for the adaptive template construction. The bone shapes are modeled in terms of an SSM by incorporating shape variations of each bone via principal component analysis (PCA). The bone poses are modeled in terms of a SPM by computing the statistical variations of the anatomical poses among the system of bones.

The SSM construction follows the work of (Luthi et al., 2018; Rueckert et al., 2003), which models the deformation field from the mean shape. The SSM of each bone is modeled separately by first aligning bone segmentations via rigid image registration. From a randomly selected segmentation reference $I_r$ in the atlas of A images, a deformable registration using free-form deformation (FFD) is performed to other segmentations in the atlas $I_a$, where a=1, 2, ..., A, a≠r, creating (N−1) deformation fields $\phi(x)$ of the form (Schnabel et al., 2001):

$$\phi(x)=\Sigma_{l=0}^{3}\Sigma_{m=0}^{3}\Sigma_{n=0}^{3}B_l(u)B_m(v)B_n(w)c_{i+l,j+m,k+n} \quad (3)$$

where c denotes a 3D lattice of control points that parametrizes the deformation field, (i, j, k) denotes the indices of the control points, and (u, v, w) denotes the relative position of voxel x in the lattice coordinates. The deformation field is a 3D tensor product of the one-dimensional cubic B-splines $B_l$, $B_m$, $B_n$. The FFD registration between two segmentations is solved using gradient descent minimization with a mean-squared-difference similarity metric. $\phi(x)$ maps each control point in the reference segmentation to the corresponding point in the target segmentation. A statistical analysis of φ(x) using PCA can model the shape variation of the bone segmentations, which is parametrized by the control point vectors c:

$$c = \bar{c} + Pv_{SSM} \tag{4}$$

where $\bar{c}$ is the average control point vector, P is the matrix composed from the SSM principal component vectors, and v SSM is the model parameter vector. Such a procedure is closely related to the standard SSM concept, which applies a PCA to corresponding points on the surface of the anatomy, but no manual definition of correspondence landmarks is required. For notational simplicity, the function relating the control points vector c to the deformation field φ (Eq. (3)) and the deformed image $I_{\rho} \circ \phi(x)$ is denoted as ψ(•). The standard deviation of the control points deformation, quantifying the variability of the SSM, is around 3.3 mm.

2.2.2 Statistical Pose Model of Anatomy in its Natural/Desired Morphology

After modeling individual bone shape via SSM, the three pelvic bones (sacrum and left/right innominate) are treated as a multi-body system in which the poses are jointly modeled via SPM. SPM is defined by the statistical variation of the poses (i.e., the similarity transformations with respect to the mean) and can be used to extrapolate the pose of a dislocated bone based on the other bone poses.

Any 3D similarity transformation can be written in homogenous coordinates as:

$$T = \begin{bmatrix} sR_{3\times3} & d \\ 0^T & 1 \end{bmatrix} \tag{5}$$

where $s \in \mathbb{R}^+$ is a scaling parameter, $R_{3\times3} \in SO(3)$ is an orthogonal rotational matrix, and $d \in \mathbb{R}^3$ is a 3D translation vector. The group of matrices following Equation (5) forms a Lie group, which is globally curved but locally linear (i.e., Euclidean in the tangent space). The Lie group and its tangent space can be inter-converted using exponential and logarithm mapping due to the following properties:

$$\exp\begin{bmatrix} 0 & 0 & 0 & t_x \\ 0 & 0 & 0 & t_y \\ 0 & 0 & 0 & t_z \\ 0 & 0 & 0 & 0 \end{bmatrix} = \begin{bmatrix} 1 & 0 & 0 & t_x \\ 0 & 1 & 0 & t_y \\ 0 & 0 & 1 & t_z \\ 0 & 0 & 0 & 1 \end{bmatrix} \tag{6a}$$

$$\exp\begin{bmatrix} 0 & -r_z & r_y & 0 \\ r_z & 0 & -r_x & 0 \\ -r_y & r_x & 0 & 0 \\ 0 & 0 & 0 & 0 \end{bmatrix} = \begin{bmatrix} R & 0 \\ 0^T & 1 \end{bmatrix} \tag{6b}$$

$$\exp\begin{bmatrix} \ln sI_3 & 0 \\ 0^T & 0 \end{bmatrix} = \begin{bmatrix} sI_3 & 0 \\ 0^T & 1 \end{bmatrix} \tag{6c}$$

where $(t_x, t_y, t_z)$ are translation parameters and $(r_x, r_y, r_z) \in SO(3)$ are rotational parameters belonging to the 3D rotation group. The tangent space of the similarity transformation can then be defined by a set of 7 parameters:

$$b = [t_x, t_y, t_z, r_x, r_y, r_z, \log s]^T \tag{7}$$

The b vector is an equivalent Euclidean space representation of the similarity transformation. Hence, any similarity transformation can be written as an exponential mapping of its orthogonal basis decomposition:

$$T = \exp\left(\sum_{i=1}^{7} [b]_i B_i\right) \tag{8a}$$

$$[B_1]_{1,4} = [B_2]_{2,4} = [B_3]_{3,4} = 1, \tag{8b}$$

$$[B_4]_{3,2} = [B_5]_{1,3} = [B_6]_{2,1} = 1,$$

$$[B_4]_{2,3} = [B_5]_{3,1} = [B_6]_{1,2} = -1,$$

$$[B_7]_{1,1} = [B_7]_{2,2} = [B_7]_{3,3} = 1, \text{ otherwise } 0$$

where $[b]_i$ denotes the $i^{th}$ component of b, and $[B]_{i,j}$ denotes the $i^{th}$ column and $j^{th}$ row of B. The orthogonal basis B shares the same form as the matrices in the exponential operation in Equation (6).

Compared to the non-linear Euler angle or transformation matrix representation, the Lie group representation of the rotational parameters is linear and thus more suitable for PCA (Fletcher et al., 2004). The b vector in the Lie group space is equivalent to the matrix representation of the similarity transformation in the Euclidean space. Hence, multi-body poses can be concatenated into a single vector B for PCA in the Lie group space:

$$B = \bar{B} + Qv_{SPM} \tag{9}$$

where $\bar{B}$ is the average pose vector, Q is the covariance matrix composed from the SPM principal component vectors, and $v_{SPM}$ is the model parameter vector. For a system of L unfractured bones, the pose of the $l^{th}$ body can hence be computed from the pose vector via exponential mapping:

$$T_{SPM}^{(l)} = \exp([\bar{B} + Qv_{SPM}]_l) \tag{10}$$

where $[\bullet]_l$ are the indices corresponding to the $l^{th}$ body and exp(•) denotes the matrix exponential operation in Equation (8a) that converts the Lie group vector to Euclidean space transformation matrix.

In estimation of the target bone pose (e.g., the unknown target pose, $B_X$, of the left innominate bone), the unknown bone pose can be estimated from the observed poses of undislocated bones $B_O$ (e.g. the sacrum and the right innominate) through an inference problem of the posterior model of the SPM (Albrecht et al., 2013):

$$\hat{v} = \operatorname*{argmin}_{v} \|B_O - [\bar{B}_c]_O - [Q_c]_O v\|^2 \text{ s.t.} |v_i| \leq \pm 3\sqrt{\lambda_i} \tag{11a}$$

$$\bar{B}_c = \bar{B} + Q([Q]_O^T[Q]_O + \sigma^2 I)^{-1} Q^T (B_O - [\bar{B}]_O) \tag{11b}$$

$$Q_c = \sigma^2 Q([Q]_O^T[Q]_O + \sigma^2 I)^{-1} Q^T \tag{11c}$$

$$B_X = [\bar{B}_c]_X + [Q_c]_X \hat{v} \tag{11d}$$

where $[\bullet]_O$ and $[\ ]_X$ are the indices of the undislocated and target bones, respectively. $\bar{B}_c$ and $Q_c$ are the posterior mean and covariance matrix adjusted based on observed poses, and $\sigma^2$ models the deviation of the inference poses from the model, computed according to (Albrecht et al., 2013). Eq. (13a) is solved using interior-point constrained optimization (Byrd et al., 2000) subject to the constraint that each entry of the SPM weight vector $v_i$ is within three standard deviations of the SPM eigenvalue $\lambda_i$.

2.2.3 Multi-Body 3D Registration

A multi-body 3D registration framework was developed for estimating the transformations of bone fragments to the desired reduction as a form of surgical planning. The registration addresses a multi-to-one problem that simultaneously solves for transformations of multiple bone fragments to align with the adaptive template and the parameters of the adaptive template to fit with the patient-specific anatomical shapes and poses. The registration is solved in the 3D image domain to take advantage of rich image information and simple inter-object operations such as intersection and union without definition of correspondence as in point- or mesh-based registrations (Albrecht and Vetter, 2012). The fracture reduction planning solves the 6 degree-of-freedom (DoF) rigid transformations T(n) for bone fragments S(n), n=1, . . . , N such that the fragments are well aligned with the adaptive template, which is modeled by SSM parameters v (l) SSM, l=1, 2, . . . , L and SPM parameters v SPM. SPM transformation matrices T (l) SPM can be obtained from v SPM via Eq. (12). The cost function C reg combines the squared difference between the adaptive template l template and the transformed bone fragments with a regularization term R to inhibit bone fragment collision/overlap:

$$C_{reg} = \|I_{template} - \Sigma_{n=1}^{N} T^{(n)}(S^{(n)})\|^2 + \lambda R \quad (12a)$$

where the adaptive template image:

$$I_{template} = \Sigma_{l=1}^{L} T_{SPM}^{(l)}(\psi(\bar{c}^{(l)} + P_{SSM}^{(l)} v_{SSM}^{(l)})) \quad (12b)$$

is the summation of L healthy bone images converted from the SSM parameters via $\psi(\cdot)$ and transformed via SPM. The regularization R is the sum of overlap between any two fragments:

$$R = \Sigma_{i=1}^{N-1} \Sigma_{j=i+1}^{N} \|T^{(i)}(S^{(i)}) \cap T^{(j)}(S^{(j)}))\|^2 \quad (12c)$$

with $\lambda$ controlling the strength of the regularization and allowing small overlap between bone fragment segmentations. For small segmentation errors at the fracture plane, such tolerance improves accuracy compared to a hard threshold that forbids any overlap. In addition, the regularization keeps the cost function smooth. Since bone fragments S are represented as 3D binary images, the overlap can be easily computed by the sum of element-wise multiplication.

TABLE 1

Alternating optimization for pelvic fracture reduction $\{T_{SPM}^{(l)} = T_{SPM}^{0(l)}\}, \{v_{SSM}^{(l)} = 0\}, \{T^{(n)} = I\}$
for t = 1 to max_iteration
  % Stage 1: Fragment Alignment Update
  Solve $\{T^{(n)}\} : \{\hat{T}^{(n)}\} = \arg\min_{\{T^{(n)}\}} C_{reg}$
  % Stage 2: SSM Adaption
  Solve $\{v_{SSM}^{(l)}\} : \{\hat{v}_{SSM}^{(l)}\} = \arg\min_{\{v_{SSM}^{(l)}\}} C_{reg}$
  % Stage 3: SPM Adaption
  Solve $\{T_{SPM}^{(l)}\}$ using Eqn 10, 11a, 11b, 11c, and 11d
End Direct minimization of Eq. (12a) is challenging due to the high dimensional, generally non-convex parameter space that is subject to local minima. To reduce the dimensionality, an alternating minimization approach is used that iteratively alternates among three stages: (1) registration of N bone fragments to the adaptive template to solve for the rigid transformations $\{T^{(n)}\}$; (2) adaptation of the template shape (parametrized by $\{v_{SSM}^{(l)}\}$ of the SSM) to patient-specific shapes; and (3) adaptation of the template poses (parametrized by $\{T_{SPM}^{(l)}\}$ of the SPM).

Stage (1) computes the rigid transformations that minimize the squared difference between the bone fragments and SSM reference. The registration solves for all fragments simultaneously to account for inter-fragment relationships. The transformations were solved simultaneously using the covariance matrix adaption evolution strategy (CMA-ES) optimizer (Hansen et al., 2003). Once the bone fragments are aligned with the current adaptive template, stage (2) adapts the SSM to the patient shape (represented by the summation of bone fragments). An interior-point constrained optimization (Byrd et al., 2000) is performed such that the SSM parameters are within three standard deviations of the SSM eigenvalues. Finally, in stage (3), the poses of the undislocated bones can be recomputed using the updated SSM, and the target poses of the dislocated bones can then be updated using Eq. (13a-b), resulting in estimation of $\{\hat{T}_{SPM}^{(l)}\}$.

Three special cases are evident. (1) Stage (2) may be omitted in cases in which a prior CT image (i.e., prior to the fracture) is available, or the contralateral bone can be assumed to provide a symmetric reference. (2) Stage (3) may be omitted in cases for which no dislocation of the overall innominate is present. (3) In case of trauma with sacral fracture, reduction planning of sacrum needs to be performed using only the SSM of the sacrum and omitting Stage (3). By assuming the sacrum is correctly reduced, reduction planning of the innominate bones can be performed following the algorithm in Table 1.

The method is initialized with the SSM mean shape of each bone aligned with the largest fragment of each pelvic bone. Other bone fragments are then rigidly registered to the residual template (the SSM mean shape subtracted by initialized bones) sequentially in the order of fragment size. The dislocated bone(s) is identified, and the initial SPM poses $\{T^{0}_{SPM}^{(l)}\}$ are computed. Table 2 summarizes the alternating optimization, with an iteration loop that cycles between fragment alignment updates, SSM, and SPM adaptation.

2.3 Multi-Body 3D-2D Registration for X-Ray, Such as Fluoroscopy-Guided 3D Navigation The multi-body 3D-2D registration follows a previously reported method (Han et al., 2020a) for intensity-based registration between multiple bone fragments and intraoperative fluoroscopy to provide fluoroscopy-guided navigation. The registration comprises two steps with the first step resolving geometry of the largest bone fragment (alternatively, any bone within the field of view of the fluoroscopy image), and the second step resolving inter-body geometry. In the first step, the system geometry is parametrized by a 9 DoF projection matrix H that describes the 3D source position, detector position, and detector rotation. Digitally reconstructed radiographs (DRRs) can be computed by forward projecting bone fragment segmentations according to H. The registration is solved by an iterative search for the parameters in H that maximize image similarity between the intraoperative fluoroscopic images P and the DRRs. In the second step, the N-body geometry parametrized by 6 DoF rigid transformations $T_{3D2D}^{(n)}$, n=1, 2, . . . , N is solved in a similar manner as in the first step with solved projection matrix H. $T_{3D2D}^{(n)}$ are defined in the preoperative CT coordinate frame and represent the transformations of the bone fragments from their preoperative poses.

The similarity metric employed in this work is based on pixelwise correspondence of gradient orientation (GO) (Lowe, 2004).

$$GO(I_1, I_2) = \frac{1}{\max(N, N_{LB})} \sum_{i \in \{\Omega : |\nabla I_1(i)| > t_1 \cap |\nabla I_2| > t_2\}} \frac{2 - \ln(|\psi_i| + 1)}{2} \quad (13)$$

where $\nabla$ denotes the gradient operator, $\psi_i$ denotes the angle between gradient vectors $\nabla I_1(i)$ and $\nabla I_2(i)$ at pixel location i, and N and $N_{LB}$ denote the number of evaluated pixels and the lower bound (half of the total pixels in the radiograph), respectively. Only pixels with gradient magnitude exceeding the threshold values $t_1$ and $t_2$ (set as the median gradient magnitude of $I_1$ and $I_2$) are evaluated.

GO has the advantage of filtering out low spatial frequency differences and focusing on the boundaries of rigid bone anatomy, while mitigating the effect of strong gradient magnitude produced by extraneous instrumentation that may be present in the fluoroscopy image, but not the CT (De Silva et al., 2016). The similarity metric is maximized using CMA-ES iterative optimization, which has demonstrated robust convergence properties in 3D-2D registration (Otake et al., 2013; Uneri et al., 2014a). The optimization problems of the first and second step are defined in Eqs. (29a) and (29b), respectively:

$$\hat{H}_\theta = \underset{H_\theta}{\mathrm{argmax}}\, GO\left(P_\theta, \int_H S^{(n)} d\vec{r}_{H_\theta}\right) \quad (14a)$$

$$\{\hat{T}_{3D2D}^{(n)}\} = \underset{\{\hat{T}_{3D2D}^{(n)}\}}{\arg\max} \sum_\theta GO\left(P_\theta, \int_{\hat{H}_\theta} T_{3D2D}^{(n)}(S^{(n)}) d\vec{r}_{\hat{H}_\theta}\right) \quad (14b)$$

where $\vec{r}_{H_\theta}$ is the ray from the x-ray source along the projection matrix $H_\theta$, for a given fluoroscopic view $\theta$. The optimization is performed in a multi-resolution fashion with image downsampling factors of [4×, 2×], CMA-ES population size of [100, 100], and CMA-ES standard deviation of [4, 1] mm and [4, 1]° following parameter selection and sensitivity analysis described in (Han et al., 2020a).

The 3D-2D registration provides an estimation of current poses of bone fragments with respect to the preoperative reduction plan. Given the registration solution of a bone that is not dislocated and not surgically reduced as $T_{3D2D}^{(0)}$ (e.g., the sacrum), the transformation needed to reduce the $l^{th}$ bone fragment to the reduction plan is $T_{3D2D}^{(n)-1} T^{(n)} T_{3D2D}^{(0)}$. FIG. 1 shows the preoperative plan transformed to the intraoperative coordinate frame and forward projected onto the fluoroscopic image for 2D augmented fluoroscopy guidance, with the plans for the two fragments highlighted in item 110. Such visualization is intended to help guide additional reduction (if required) to achieve the target plan in a view (i.e., the fluoroscopy image) that is familiar to orthopaedic surgeons. In addition, as shown in FIG. 1, the current and planned poses of bone fragments can be visualized in a 3D view similar to a conventional 3D surgical navigation system, where the 3D surfaces associated with the reduction plan are shown relative to the poses of each fragment as solved by 3D-2D registration. The poses of the undislocated bone fragments can also be visualized. From such 3D views, the 6 DoF reduction needed to restore each bone fragment to its desired pose can be qualitatively and quantitatively obtained.

Figure 3A:
FIG. 3A, FIG. 3B, and FIG. 3C show a multi-body 3D-2D registration and guidance according to examples of the present teachings.
Figure 3B:
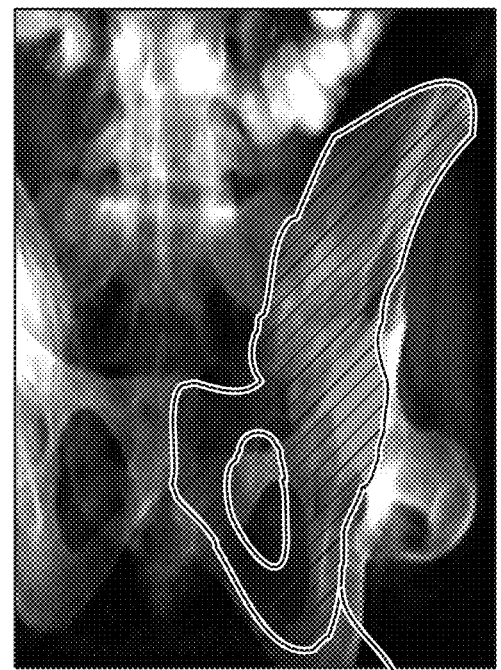
Figure 3C:
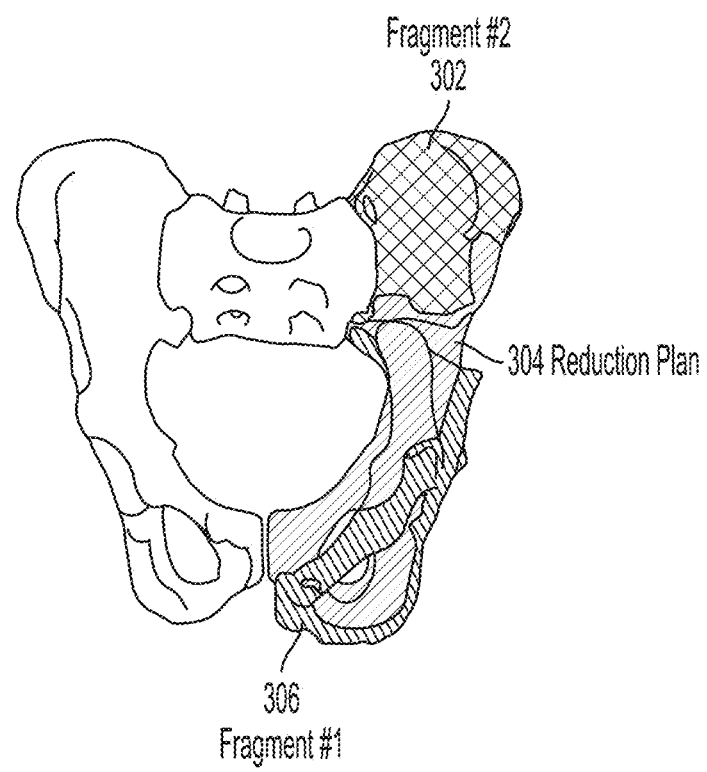

FIG. 3A, FIG. 3B, and FIG. 3C show a multi-body 3D-2D registration and guidance according to examples of the present teachings. FIG. 3A shows an AP x-ray image, such as a fluoroscopic image, of a pelvis with left innominate fracture (two-body fracture at the ilium wing). The DRR Canny edges 302 of the two fragments, the right innominate and sacrum registration overlaid on the x-ray image, such as a fluoroscopic image, show close alignment. FIG. 3B shows the x-ray image, such as the fluoroscopic image, is augmented with a projection 304 of the preoperative reduction plan of the two fragments using the resulting 3D-2D registration. The current state of the patient relative to the target reduction and possible further reduction can be visualized. FIG. 3C shows a 3D visualization of the intraoperative bone positions 302 and 306 overlaid with the reduction planning 304.

In summary, an alternating registration framework is provided for planning and guidance of reduction of multiple anatomical structures to a desired orientation. The "planning" aspect uses a combination of SSM and SPM. The "guidance" aspect registers the desired pose as determined in a 3D image (e.g., preoperative CT) to a 2D image (e.g., one or more intraoperative radiographs). The multiple structures can relate to abnormal anatomical structures (e.g., fractured bone fragments), to anatomy with multiple components (e.g., the spine), and/or to one or more anatomical structures and one or more surgical instruments.

The registration framework is illustrated in the specific (preferred) embodiment of pelvic reduction planning to simultaneously register bone fragment segmentations onto an adaptive template. The method is suitable to registration of multiple bone fragments (e.g., multiple bone components in the pelvic trauma scenario detailed above), and the "adaptive template" concept is such that the template is adapted in the course of the alternating registration to the patient-specific shape and pose.

Aspects of the present disclosure include: (1) combination of SSMs and SPMs as templates for multi-body reduction planning; (2) a cost function for multi-body ("many-to-one") registration based on differences between the adaptive template and bone fragment positions (regularized to avoid overlap/collision); and (3) registration of the planned reduction to the intraoperative scene via 3D-2D multi-body registration based on one or more 2D x-ray views, such as 2D fluoroscopic views. The result allows visualization of the planned reduction relative to intraoperative x-ray, such as fluoroscopy and/or preoperative CT. The method has been tested in simulation, phantom studies, and initial clinical studies and demonstrates accuracy of registration consistent with clinical requirements.

Additional aspects of the disclosure can be applied to field of plastic surgery and congenital disorders/birth defects. An atlas can reference the spectrum of "normal" or desire anatomical setups and the multi-body registration can work off the current anatomical constellation of a piecewise anatomy or fragments as suggested by the surgeon.

Further aspects of the disclosure provide for a certain fragmentation semi or fully automatically of existing unfavorable anatomy of the patient within limitations of the surgical field to achieve a certain outcome for a fracture reduction fitting within a desire atlas. The present automatic fragment alignment and template adaptation allow the surgeon to quickly simulate several scenarios.

Figure 4:
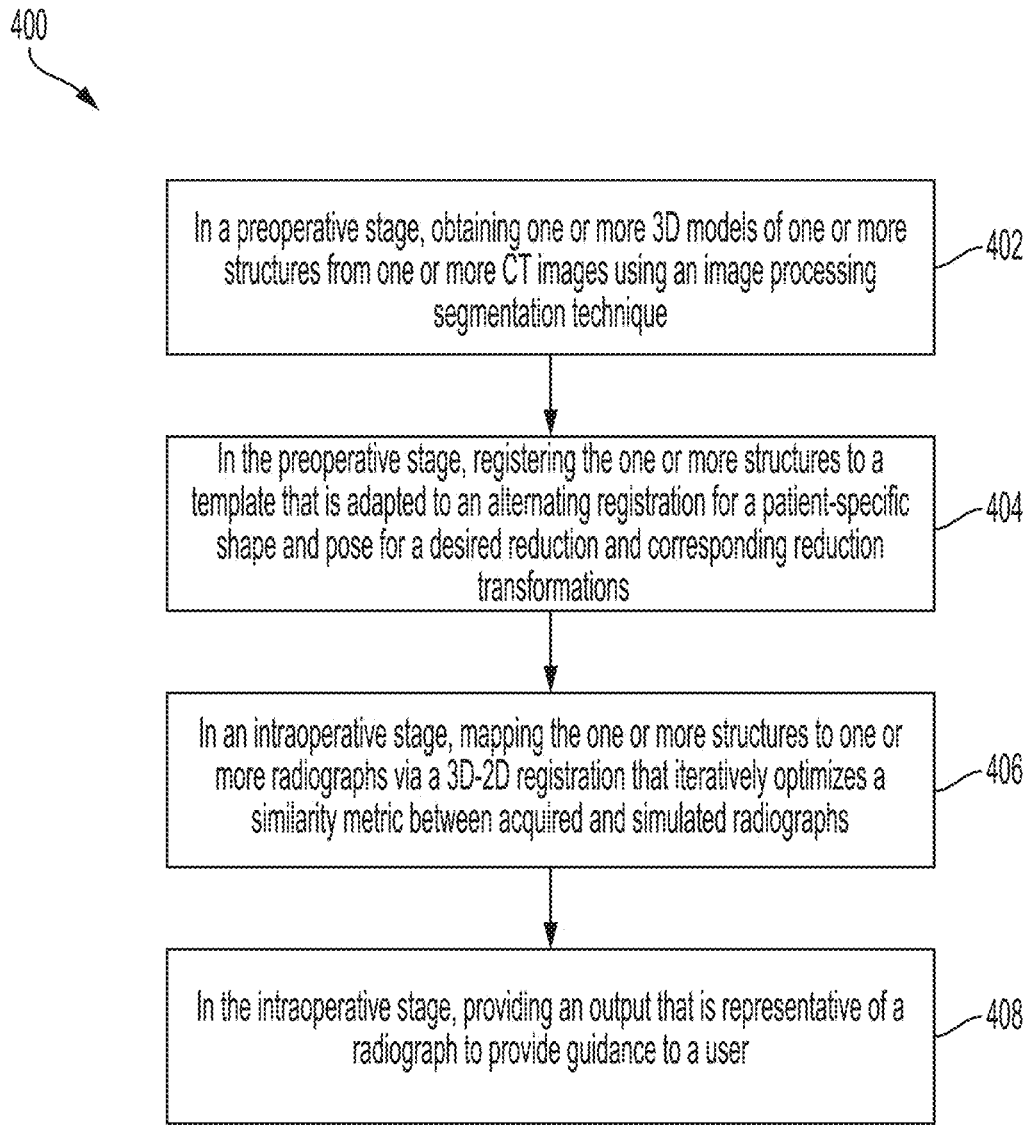
FIG. 4 shows a method 400 for registering one or more structures to a desired orientation for planning and guidance for surgery, according to examples of the present disclosure.

FIG. 4 shows a method 400 for registering one or more structures to a desired orientation for planning and guidance for surgery, according to examples of the present disclosure. The method 400 comprises in a preoperative stage, obtaining one or more 3D models of one or more structures from one or more CT images using an image processing segmentation technique or a manual segmentation technique at 402. The one or more structures can comprise one or more anatomical structures, an anatomy with multiple components, one or more anatomical structures and one or more surgical instruments, and combinations thereof. The multiple components can comprise one or more bone fragment components. In some examples, the image processing segmentation techniques comprises a max-flow min-cut segmentation technique.

The method 400 continues in the preoperative stage, registering the one or more structures to a template that is adapted to an alternating registration for a patient-specific shape and pose for a desired reduction and corresponding reduction transformations at 404. The template is based on a statistical shape model and a statistical pose model. The registering comprises computing a cost function for multi-body registration based on a disparity between the template and positions of the one or more structures. In some examples, the one or more structures can comprise multiple bone fragments of a pelvis and the cost function is computed based on a disparity between a pelvis template and the multiple bone fragments. In some examples, the cost function is further computed based on a fragment collision regularization. In some examples, the disparity is a squared difference.

The method 400 continues in an intraoperative stage, mapping the one or more structures to one or more radiographs via a 3D-2D registration that iteratively optimizes a similarity metric between acquired and simulated radiographs at 406.

The method 400 continues in the intraoperative stage, providing an output that is representative of a radiograph to provide guidance to a user at 408. The output can comprise a 2D x-ray image, such as a 2D fluoroscopic scene or a 3D shape representation of the anatomy as evident in the 2D x-ray image, such as a 2D fluoroscopy view.

Figure 5:
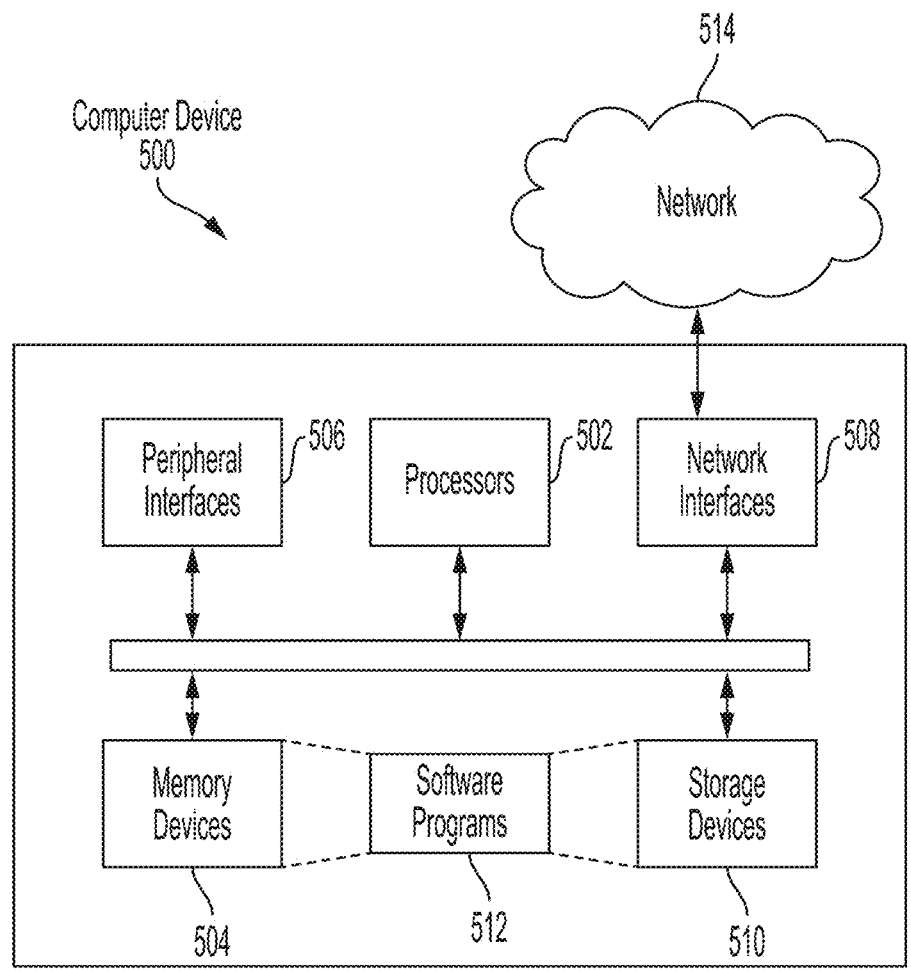
FIG. 5 is an example of a hardware configuration for computer device, according to examples of the present disclosure.

FIG. 5 is an example of a hardware configuration for computer device 500, which can be used to perform one or more of the processes described above. Computer device 500 can be any type of computer devices, such as desktops, laptops, servers, etc., or mobile devices, such as smart telephones, tablet computers, cellular telephones, personal digital assistants, etc. As illustrated in FIG. 5, computer device 500 can include one or more processors 502 of varying core configurations and clock frequencies. Computer device 500 can also include one or more memory devices 504 that serve as a main memory during the operation of computer device 500. For example, during operation, a copy of the software that supports the above-described operations can be stored in one or more memory devices 504. Computer device 500 can also include one or more peripheral interfaces 506, such as keyboards, mice, touchpads, computer screens, touchscreens, etc., for enabling human interaction with and manipulation of computer device 500.

The computer device 500 can also include one or more network interfaces 508 for communicating via one or more networks, such as Ethernet adapters, wireless transceivers, or serial network components, for communicating over wired or wireless media using protocols. Computer device 500 can also include one or more storage devices 510 of varying physical dimensions and storage capacities, such as flash drives, hard drives, random access memory, etc., for storing data, such as images, files, and program instructions for execution by one or more processors 502.

Additionally, Computer device 500 can include one or more software programs 512 that enable the functionality described above. One or more software programs 512 can include instructions that cause one or more processors 502 to perform the processes, functions, and operations described herein, for example, with respect to the processes of FIG. 4. Copies of one or more software programs 512 can be stored in one or more memory devices 504 and/or on in one or more storage devices 510. Likewise, the data utilized by one or more software programs 512 can be stored in one or more memory devices 504 and/or on in one or more storage devices 510.

In implementations, Computer device 500 can communicate with other devices via network 514. The other devices can be any types of devices as described above. Network 514 can be any type of network, such as a local area network, a wide-area network, a virtual private network, the Internet, an intranet, an extranet, a public switched telephone network, an infrared network, a wireless network, and any combination thereof. Network 514 can support communications using any of a variety of commercially-available protocols, such as TCP/IP, UDP, OSI, FTP, UPnP, NFS, CIFS, AppleTalk, and the like. Network 514 can be, for example, a local area network, a wide-area network, a virtual private network, the Internet, an intranet, an extranet, a public switched telephone network, an infrared network, a wireless network, and any combination thereof.

Computer device 500 can include a variety of data stores and other memory and storage media as discussed above. These can reside in a variety of locations, such as on a storage medium local to (and/or resident in) one or more of the computers or remote from any or all of the computers across the network. In some implementations, information can reside in a storage-area network ("SAN") familiar to those skilled in the art. Similarly, any necessary files for performing the functions attributed to the computers, servers, or other network devices may be stored locally and/or remotely, as appropriate.

In implementations, the components of computer device 500 as described above need not be enclosed within a single enclosure or even located in close proximity to one another. Those skilled in the art will appreciate that the above-described componentry are examples only, as computer device 500 can include any type of hardware componentry, including any necessary accompanying firmware or software, for performing the disclosed implementations. Computer device 500 can also be implemented in part or in whole by electronic circuit components or processors, such as application-specific integrated circuits (ASICs) or field-programmable gate arrays (FPGAs).

If implemented in software, the functions can be stored on or transmitted over a computer-readable medium as one or more instructions or code. Computer-readable media includes both tangible, non-transitory computer storage media and communication media including any medium that facilitates transfer of a computer program from one place to another. A storage media can be any available tangible, non-transitory media that can be accessed by a computer. By way of example, and not limitation, such tangible, non-transitory computer-readable media can comprise RAM, ROM, flash memory, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes CD, laser disc, optical disc, DVD, floppy disk and Blu-ray disc where disks usually reproduce data magnetically, while discs reproduce data optically with lasers. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Combinations of the above should also be included within the scope of computer-readable media.

The foregoing description is illustrative, and variations in configuration and implementation can occur to persons skilled in the art. For instance, the various illustrative logics, logical blocks, modules, and circuits described in connection with examples of the present disclosure disclosed herein can be implemented or performed with a general purpose processor, a digital signal processor (DSP), an application specific integrated circuit (ASIC), a field programmable gate array (FPGA), cryptographic co-processor, or other programmable logic device, discrete gate or transistor logic, discrete hardware components, or any combination thereof designed to perform the functions described herein. A general-purpose processor can be a microprocessor, but, in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

In one or more examples, the functions described can be implemented in hardware, software, firmware, or any combination thereof. For a software implementation, the techniques described herein can be implemented with modules (e.g., procedures, functions, subprograms, programs, routines, subroutines, modules, software packages, classes, and so on) that perform the functions described herein. A module can be coupled to another module or a hardware circuit by passing and/or receiving information, data, arguments, parameters, or memory contents. Information, arguments, parameters, data, or the like can be passed, forwarded, or transmitted using any suitable means including memory sharing, message passing, token passing, network transmission, and the like. The software codes can be stored in memory units and executed by processors. The memory unit can be implemented within the processor or external to the processor, in which case it can be communicatively coupled to the processor via various means as is known in the art.

While the preferred embodiments have been shown and described, it will be understood that there is no intent to limit the invention by such disclosure, but rather, is intended to cover all modifications and alternate constructions falling within the spirit and scope of the invention.

What is claimed is:

1. A method for registering one or more structures to a desired orientation for planning and guidance for surgery, the method comprising:
   in a preoperative stage, obtaining one or more 3D models of one or more structures from one or more CT images using an image processing segmentation technique or a manual segmentation technique;
   in the preoperative stage, registering the one or more structures to a template that is adapted to an alternating registration for a patient-specific shape and pose for a desired reduction and corresponding reduction transformations, wherein the registering comprises computing a cost function for multi-body registration based on a disparity between the template and positions of the one or more structures and wherein the cost function is further computed based on a fragment collision regularization;
   in an intraoperative stage, mapping the one or more structures to one or more radiographs via a 3D-2D registration that iteratively optimizes a similarity metric between acquired and simulated radiographs; and
   in the intraoperative stage, providing an output that is representative of a radiograph or a 3D tomographic representation to provide guidance to a user.

2. The method of claim 1, wherein the one or more structures comprise one or more anatomical structures, an anatomy with multiple components, one or more anatomical structures and one or more surgical instruments, and combinations thereof.

3. The method of claim 2, wherein the multiple components comprise one or more bone fragment components.

4. The method of claim 1, wherein the template is based on a statistical shape model and a statistical pose model.

5. The method of claim 1, wherein the output comprises a 2D x-ray image or a 3D shape representation of the anatomy as evident in the 2D x-ray image.

6. The method of claim 1, wherein the one or more structures comprise multiple bone fragments of a pelvis or another multi-bone anatomy structure and the cost function is computed based on a disparity between a pelvis template and the multiple bone fragments.

7. The method of claim 6, wherein the cost function is further computed based on a fragment collision regularization or a disparity between a template of a joint and multiple bone components.

8. The method of claim 6, wherein the disparity is a squared difference or a disparity between a template of a joint and multiple bone component.

9. The method of claim 1, wherein the image processing segmentation techniques comprises a max-flow min-cut segmentation technique, an image processing segmentation technique, or a manual segmentation technique.

10. A computer system comprising:
    a hardware processor;
    a non-transitory computer readable medium comprising instructions that when executed by the hardware processor perform a method for registering one or more structures to a desired orientation for planning and guidance for surgery, the method comprising:
    in a preoperative stage, obtaining one or more 3D models of one or more structures from one or more CT images using an image processing segmentation technique or a manual segmentation technique;
    in the preoperative stage, registering the one or more structures to a template that is adapted to an alternating registration for a patient-specific shape and pose for a desired reduction and corresponding reduction transformations, wherein the registering comprises computing a cost function for multi-body registration based on a disparity between the template and positions of the one or more structures and wherein the cost function is further computed based on a fragment collision regularization;
    in an intraoperative stage, mapping the one or more structures to one or more radiographs via a 3D-2D registration that iteratively optimizes a similarity metric between acquired and simulated radiographs; and
    in the intraoperative stage, providing an output that is representative of a radiograph or a 3D tomographic representation to provide guidance to a user.

11. The computer system of claim 10, wherein the one or more structures comprise one or more anatomical structures, an anatomy with multiple components, one or more anatomical structures and one or more surgical instruments, and combinations thereof.

12. The computer system of claim 11, wherein the multiple components comprise one or more bone fragment components.

13. The computer system of claim 10, wherein the template is based on a statistical shape model and a statistical pose model.

14. The computer system of claim 10, wherein the output comprises a 2D x-ray image or a 3D shape representation of the anatomy as evident in the 2D x-ray image.

15. The computer system of claim 10, wherein the one or more structures comprise multiple bone fragments of a pelvis and the cost function is computed based on a disparity between a pelvis template and the multiple bone fragments.

16. A non-transitory computer readable medium comprising instructions that when executed by a hardware processor perform a method for registering one or more structures to a desired orientation for planning and guidance for surgery, the method comprising:
- in a preoperative stage, obtaining one or more 3D models of one or more structures from one or more CT images using an image processing segmentation technique or a manual segmentation technique;
- in the preoperative stage, registering the one or more structures to a template that is adapted to an alternating registration for a patient-specific shape and pose for a desired reduction and corresponding reduction transformations, wherein the registering comprises computing a cost function for multi-body registration based on a disparity between the template and positions of the one or more structures and wherein the cost function is further computed based on a fragment collision regularization;
- in an intraoperative stage, mapping the one or more structures to one or more radiographs via a 3D-2D registration that iteratively optimizes a similarity metric between acquired and simulated radiographs; and
- in the intraoperative stage, providing an output that is representative of a radiograph or a 3D tomographic representation to provide guidance to a user.

17. The non-transitory computer readable medium of claim 16, wherein the one or more structures comprise one or more anatomical structures, an anatomy with multiple components, one or more anatomical structures and one or more surgical instruments, and combinations thereof.

18. The non-transitory computer readable medium of claim 17, wherein the multiple components comprise one or more bone fragment components.

19. The non-transitory computer readable medium of claim 16, wherein the template is based on a statistical shape model and a statistical pose model.

20. The non-transitory computer readable medium of claim 16, wherein the output comprises a 2D x-ray image or a 3D shape representation of the anatomy as evident in the 2D x-ray image.

* * * * *